(12) United States Patent
Esterowitz et al.

(10) Patent No.: US 6,358,243 B1
(45) Date of Patent: Mar. 19, 2002

(54) DUAL WAVELENGTH SURGICAL LASER SYSTEM

(75) Inventors: Leon Esterowitz, Springfield; Charles L. Marquardt, Great Falls, both of VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 1081 days.

(21) Appl. No.: 08/511,341

(22) Filed: Aug. 4, 1995

(51) Int. Cl.[7] ............................................. A61B 18/20
(52) U.S. Cl. ............................... 606/10; 606/3; 606/13
(58) Field of Search ...................................... 606/2–19

(56) References Cited

U.S. PATENT DOCUMENTS 5,312,396 A * 5/1994 Feld et al. ..................... 606/3

* cited by examiner

Primary Examiner—David M. Shay

(57) ABSTRACT

A dual wavelength surgical laser system for performing laser surgery on living tissue with a minimum amount of collateral tissue damage is disclosed. The dual wavelength surgical laser system comprises: a pump laser for emitting pump laser pulses of light at a preselected pump wavelength; an optical parametric oscillator responsive to each pump pulse from the pump laser for producing a first wavelength pulse of light in a water absorption band of the tissue and a second wavelength pulse of light in a protein absorption band of the tissue; a first set of optics for only passing therethrough each first wavelength pulse from the optical parametric oscillator; an optical delay line for delaying each first wavelength pulse from the first set of optics by a predetermined period of time; a second set of optics for only passing therethrough each second wavelength pulse from the optical parametric oscillator; and a beam combiner for combining each second wavelength pulse with the following delayed first wavelength pulse to form a stream of consecutive second and delayed first pulse pairs for application to the tissue.

23 Claims, 4 Drawing Sheets

DUAL WAVELENGTH SURGICAL LASER SYSTEM

1. FIELD OF THE INVENTION

The present invention relates to lasers and particularly to a dual wavelength surgical laser system that would inflict significantly less collateral tissue damage during surgery than currently available scalpels or medical lasers.

2. DESCRIPTION OF THE RELATED ART

Lasers are currently employed in a wide variety of surgical applications. A major disadvantage encountered in laser surgery is collateral tissue damage. Such damage frequently results in longer healing times, accompanied by an increase in scarring. It has been fairly well established that collateral damage is caused by thermal diffusion and/or shock waves, and efforts have been made to reduce the damage by judicious selection of laser wavelength and pulse width. Until very recently, tissue ablation models employed in that selection process were based on a detailed understanding of the properties of water. Although water is the principal constituent of all biological tissue, it does not determine all the physical properties involved in the tissue ablation mechanism. Mechanical properties in particular are determined primarily by protein constituents such as collagen, lipoproteins and proteoglycans. With the availability of the medical free electron laser (FEL) at Vanderbilt University Medical Center (VUMC) it has now become possible to investigate the role played by the protein constituents in the laser tissue ablation process. This is accomplished by irradiating into known amide absorption bands in the spectral region between 5.9 $\mu$m and 6.6 $\mu$m, which have varying degrees of overlap with the absorption due to the bending mode of water. In a most recent FEL study of corneal, dermal and neural tissue, which covered the spectral range between 2.5 $\mu$m and 6.85 $\mu$m, VUMC scientists observed maximum ablation rate and minimum collateral damage when they tuned to the amide-II band near 6.45 $\mu$m.

These exciting new FEL results have raised several basic questions about the fundamental mechanism of laser ablation, and they suggest the possibility of designing a surgical laser which could inflict significantly less collateral tissue damage during surgery. VUMC scientists have proposed a dual-mechanism model to explain their FEL results. Qualitatively, their model assumes that laser energy absorbed into the protein and into the water perform two separate functions. The former serves to weaken the mechanical structure of the irradiated tissue volume, and the latter provides the "thermal explosion" to blow out the structurally weakened material. The highly favorable results obtained for FEL ablation of corneal tissue were tentatively attributed to the approximately equal partition of absorbed 6.45 $\mu$m radiation between the protein and the water. If this interpretation is correct, then it may also be possible to obtain even more favorable results by optimizing the partition of the absorbed energy. There has not yet been any clear indication that equipartition is optimal, nor that one specific partition of the energy will be favorable for all tissue types.

At the present time, applicants know of no prior art dual wavelength surgical laser used for precision surgery.

SUMMARY OF THE INVENTION

It is therefore an object of the invention to provide a surgical laser that would inflict significantly less collateral tissue damage during surgery than currently available scalpels or medical lasers.

Another object of the invention is to provide a dual wavelength surgical laser system for performing laser surgery on living tissue with a minimum amount of collateral tissue damage.

Another object of the invention is to provide a tunable dual wavelength surgical laser system for producing a sequence of protein and water absorption light pulse pairs, with each protein absorption light pulse softening the tissue and the following water absorption light pulse in a pulse pair acting to remove the softened tissue.

Another object of the invention is to provide a dual wavelength surgical laser system for producing a sequence of protein and water absorption light pulse pairs in which the ratio of light amplitudes in each pulse pair can be changed to compensate for a different type of living tissue having laser surgery performed thereon.

A further object of the invention is to provide a tunable, amplitude-variable, dual wavelength surgical laser system for performing laser surgery on different types of living tissue with a minimum of collateral tissue damage.

These and other objects of this invention are achieved by providing a dual wavelength surgical laser system comprising: a pump laser for emitting pump laser pulses of light at a preselected pump wavelength; an optical parametric oscillator responsive to each pump pulse from the pump laser for producing a first wavelength pulse of light in a water absorption band of the tissue and a second wavelength pulse of light in a protein absorption band of the tissue; a first set of optics for only passing therethrough each first wavelength pulse from the optical parametric oscillator; an optical delay line for delaying each first wavelength pulse from the first set of optics by a predetermined period of time; a second set of optics for only passing therethrough each second wavelength pulse from the optical parametric oscillator; and a beam combiner for combining each second wavelength pulse with the following delayed first wavelength pulse to form a stream of consecutive second and delayed first pulse pairs for application to the tissue.

BRIEF DESCRIPTION OF THE DRAWINGS

These and other objects, features and advantages of the invention, as well as the invention itself, will become better understood by reference to the following detailed description when considered in connection with the accompanying drawings wherein like reference numerals designate identical or corresponding parts throughout the several views and wherein:

FIG. 3 is a graph illustrating the protein and water absorption lines from the OPO of FIG. 1 for the tuning angle of 47.3 degrees shown in FIG. 2.

DETAILED DESCRIPTION OF THE PREFERRED EMBODIMENT

Before the invention is explained in detail, a brief overview of the operation of the invention will now be provided to aid in the understanding of the invention.

The phase matching angle of a tunable nonlinear crystal in the dual wavelength surgical laser system of the invention is adjusted to simultaneously produce a protein band light pulse and a water band light pulse at different wavelengths to enable independent irradiations into the water absorption band and the protein absorption band of tissue during laser surgery. The irradiation into the protein band softens the mechanical structure of the tissue, while the water irradiation produces what is called a "thermal explosion" of the tissue to push the tissue out. An adjustable delay line in the path of the water band light pulse is adjusted to vary the delay between the protein and water band light pulses in order to allow an optimal time for thermal relaxation of the mechanical structure once it has been excited by the protein band light pulse before the associated water band light pulse is applied. In order to account for the different requirements for different types of tissue on which to operate, the amplitude of the water band light pulse can be attenuated by an adjustable attenuator disposed in the water absorption line to obtain a different ratio of water absorption light to protein absorption light. A sequence of pairs of different light pulses, with each pair comprised of a protein band light pulse followed by a water band light pulse, are then fed into a fiber delivery system (not shown) for surgical application.

Figure 1:
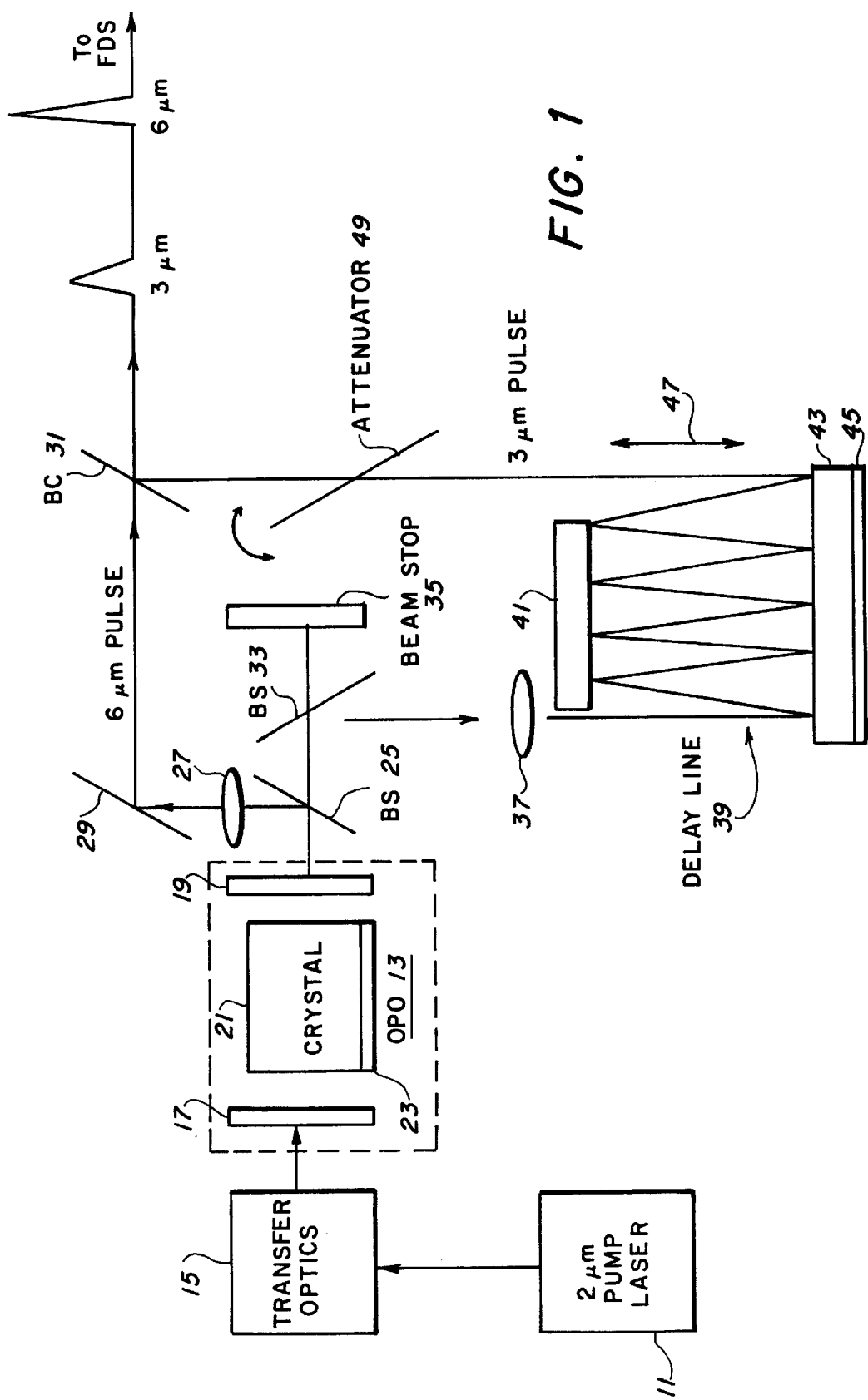
FIG. 1 shows a schematic diagram of a preferred embodiment of the dual wavelength surgical laser system of the invention.

Referring now to the drawings, FIG. 1 shows a schematic diagram of a preferred embodiment of the dual wavelength surgical laser system of the invention.

An exemplary Q-switched 2 $\mu$m pump laser 11 is utilized to develop exemplary 2.05 $\mu$m pump pulses. The Q-switched pump laser 11 can be of the Q-switched Ho:YLF 2 $\mu$laser type described by C. L. Marquardt et al. in *J. Appl. Phys.*, Vol. 54 (10), pp.5645–5646 (Oct. 1983). However, it should be understood that any other suitable type of Q-switched laser pump source around 2 $\mu$m can be used to produce the pump pulses. More particularly, the proper selection of a laser pump source would be required to optimize the surgery on any given tissue type to reduce collateral tissue damage by the judicious selection of laser wavelength and pulse width.

The 2 $\mu$m pump pulses from the pump laser 11 are utilized to pump am optical parametric oscillator (OPO) 13. However, unless the OPO 13 is properly positioned in the beam path of the pump pulses and the pump pulses incident on the OPO 13 have the proper beam size and polarization, transfer optics 15 are required between the pump laser 11 and the OPO 13 to transfer the pump pulse light to the OPO 13 with the beam size and polarization needed for operation of the OPO 13. It should be noted at this time that both transfer optics and optical parametric oscillators are well known in the art.

The transfer optics 15 include whatever optics are required to transfer the pump pulse light from the pump laser 11 to the OPO 13 with the beam size and polarization needed for OPO operation. Anyone skilled in the laser art would be able to assemble the transfer optics 15 from standard optical components. One exemplary basic type of transfer optics 15 could include a passive turning mirror (not shown) for turning the beam at a right angle and a passive lens (not shown) for focusing the beam from the turning mirror into the OPO 13 with a desired beam size and polarization. The turning mirror could be any type of dielectric mirror which is coated for high reflectance (HR) at 2.05 $\mu$m (which is the wavelength of the pump pulses from the pump laser 11) and is positioned to have a 45 degree angle of incidence. The lens could be a single lens comprised of a fused silica substrate, be antireflective (AR) coated at 2.05 $\mu$m and have a focal length (f.l.) of about 50 centimeters (cm).

The OPO 13 is placed at an appropriate position in the path of the focused beam from the training optics 15 to obtain the proper beam diameter. The OPO 13, in its simplest form, is comprised of mirrors 17 and 19 and a nonlinear optical crystal or nonlinear crystal 21. Examples of nonlinear crystals that may be used in the OPO 13 are silver-gallium-selenide ($AgGaSe_2$) and zinc-germanium-phosphide ($ZnGeP_2$). However, the preferred nonlinear crystal 21 is $AgGaSe_2$ because of its current availability and usual degree of optical perfection. The crystal 21 is mounted on a rotation stage 23 to permit adjustment of the phase-matching angle to tune the two wavelength outputs of the nonlinear crystal 21 (to be discussed). The rotation stage 23 is available from any vender of optical hardware listed in Laser Focus Buyers' Guide (LFBG). The $AgGaSe_2$ crystal is available from Cleveland Crystals, Inc. in Cleveland, Ohio. It should be realized that a rotation stage 23 may not be needed, if the exact output wavelengths (and particularly the exact protein absorption band—to be explained) is known and the OPO 13 is constructed with a high enough degree of precision to not require any adjustment.

The mirrors 17 and 19 in the OPO 13 can be obtained from any competent IR (infrared) coating house, but the mirrors 17 and 19 actually used in the OPO 13 of FIG. 1 were specifically obtained from Laser optics, Inc. with the following indicated specifications. Mirror 17 has a fused silica substrate, a 10 meter radius of curvature (10 M RoC), a transmission better than 93% at the pump wavelength of 2.05 $\mu$m, and a reflectance greater than 99% at 3.01 $\mu$m. Mirror 19, the output coupler, has a ZnSe substrate, is flat on both sides, and has a transmission better than 90% at 2.05 $\mu$m, a reflectance of about 90% at 3.01, and a transmission of about 85% at 6.45 $\mu$m.

In operation, focused 2.05 $\mu$m pump pulses from the pump laser 11 are directed by the transfer optics 15 into the OPO 13. These 2.05 $\mu$m pump pulses are transmitted through mirror 17 into the nonlinear $AgGaSe_2$ crystal 21. In response to the 2.05 $\mu$m pump pulses the $AgGaSe_2$ crystal 21 generates two different wavelengths that are tunable between 2.65 $\mu$m and 12 $\mu$m by rotating the rotation stage 23 and, hence, the crystal 21 to a desired angle or phase matching angle (to be discussed more fully in relation to FIG. 2). In other words, for any given angle that is selected for a particular pump wavelength, the crystal 21 in the OPO 13 will develop two different wavelengths which will outputted from the OPO 13.

The rotation stage 23 can be rotated by means such as a motor (not shown) or a thumb screw (not shown) or any other suitable means for rotating the stage 23. As a result, the rotation of the crystal 21 can adjust the phase matching angle of the nonlinear $AgGaSe_2$ crystal 21 to an exemplary angle of about 47.3 degrees so that it simultaneously generates light at two different wavelengths (the idler and signal wavelengths) at 2.8 $\mu$m and 6.45 $\mu$m respectively.

It should be noted at this time that the crystal 21 could also be tuned to produce a different pair of wavelengths that could be angle-tuned over a different range of wavelengths by utilizing a different type of pump laser 11 to produce a different pump wavelength.

The signal wavelength light can also be called protein band light, protein absorption band light or protein band absorption light because it is a band of wavelengths in the tissue that has a protein absorption. The idler wavelength light can also be called water band light, water absorption band light or water band absorption light because it is a band of wavelengths in which the tissue has a water absorption.

The protein band light at 6.45 μm and the water band light at 2.8 μm, as well as the pump light at 2.05 μm, are all transmitted through the mirror or output coupler 19, as discussed before, to a beam splitter (BS) 25. The beam splitter 25 has a ZnSe substate, is flat on both sides, is anti-reflective coated at both 2.05 μm and 3.01 μm, and is highly reflective at 6.45 μm for S-polarization (S-pol) at 45 degrees angle of incidence.

As a result, the protein band light pulses at 6 micron or 6.45 μm is reflected off the beam splitter 25 and passed through a refocusing lens 27. The refocusing lens 27 has a ZnSe substrate and is anti-reflectance coated at 6.45 μm to refocus and pass the 6.45 μm light pulses to a flat mirror 29 which is highly reflective at 6.45 μm. The 6.45 μm light pulses reflected off the flat mirror 29 are then passed to a beam combiner (BC) 31 (to be discussed).

In order to obtain protein band light pulses at, for example, an exemplary wavelength of 6.45 μm, the reflected protein band light pulses from the mirror 29 can be monitored by a spectrometer (not shown) while the crystal 21 is being angletuned until the desired wavelength is detected. As will be seen in the discussion of FIG. 2, the wavelength of the water band light pulses will change very little in relation to the protein band light as the crystal 21 is being angle-tuned.

Referring back to the beam splitter 25, it will be recalled that the beam splitter 25 is anti-reflective coated at both 2.05 m and 3.01 μm. As a result, both the 2.05 μm and 3.01 μm light will pass through the beam splitter 25 to another beam splitter 33.

Beam splitter 33 has a ZnSe substrate, is flat on both of its sides, is anti-reflective coated for both 2.05 μm and 6.45 m, and is highly reflective at 3.01 μm for S-polarization (S-pol) at 45 degrees angle of incidence. As a result, any residual 2.05 μm light and any residual 6.45 μm light will pass through the beam splitter 33 and be dissipated by an exemplary carbon beam stop 35. On the other hand, the water band light pulses at 3 microns or 3.01 μm light pulses are reflected off the beam splitter 33 and passed through a refocusing lens 37. The refocusing lens 37 for the 3.01 μm light has a ZnSe substrate and is anti-reflectance coated at 3.01 μm to refocus and pass the 3.01 μm light pulses to an optical delay line 39 comprised of opposing flat mirrors 41 and 43.

It should be recalled at this time that the dual wavelength surgical laser system of the invention simultaneously produces two different wavelengths to enable independent irradiations into the water absorption band and the protein absorption band of tissue during laser surgery. The irradiation into the protein band softens the mechanical structure of the tissue, while the water irradiation produces what is called a "thermal explosion" of the tissue to push the tissue out. However, it is important to allow some time for thermal relaxation of the mechanical structure once it has been excited by a protein band light pulse before an associated water band light pulse is applied. This is accomplished by introducing a time delay between the protein band light pulse and its associated water band light pulse.

It has been discussed above that the protein band light pulse at 6.45 μm was developed and applied to the beam combiner 31, and that the water band light at 3.01 μm was simultaneously developed and applied to the optical delay line 39. It is the delay line 39 which will provide the optimum delay to the water band light pulse after the protein band light pulse has been applied to start softening the protein absorption band in the tissue or mechanical structure before the delayed water band light pulse is applied to the water absorption band in the tissue to dislodge the weakened mechanical structure.

Each of the flat mirrors 41 and 43 is highly reflective at 3.01 μm. The water band light from the lens 37 strikes one end of the mirror 43 and bounces back and forth between the mirrors 41 and 43 before exiting the delay line 39 from the mirror 43 and traveling to an adjustable attenuator 49 disposed in the water absorption line or beam path of the exiting delayed 3 μm or 3.01 μm water band light pulses.

The mirror 43 is mounted on a translation stage 45 which is moved in the directions of the double arrows 47 by, for example, a screw (not shown) or electric motor (not shown) to change the total optical delay time to a desired optical delay by shortening or lengthening the optical path between the mirrors 41 and 43.

The adjustable attenuator comprises a half wave plate (not shown) for a wavelength of 3.01 μm followed by a linear polarizer (not shown). Both of the half wave plate and polarizer components are anti-reflective coated at 3.01 μm and may be obtained from any competant IR coating house. The half wave plate is mounted on a simple rotator (not shown). The attenuation of the adjustable attenuator can be adjusted by changing the rotational position of the attenuator by means of the simple rotator, as indicated by the double arrows 51.

The adjustable attenuator 49 is needed in order to account for the different requirements for the different types of tissue on which laser surgery can be performed. The amplitude of the delayed water band light pulse can be attenuated by the adjustable attenuator 49 to obtain a different ratio of water absorption light to protein absorption light. This ratio is important because of the medical requirement for minimal invasive surgery. It is desirable to inflict the least amount of collateral damage to the human body during laser surgery. So it is highly desirable to use the absolute lowest amount of laser energy that can be used at the water band wavelength because it is this wavelength that destroys the tissue undergoing laser surgery.

A resultant sequence of attenuated, delayed water band light pulses at 3.01 μm is applied from the attenuator 49 to the beam combiner 31. It should be recalled that a sequence of undelayed protein band light pulses at 6.45 μm is also being applied to the beam combiner 31. As a consequence, the beam combiner 31 combines the sequence of delayed water band light pulses with the sequence of undelayed protein band light pulses to develop a sequence of pairs of different light pulses, with each pair comprised of a protein band light pulse followed by a water band light pulse. This sequence of pairs of protein band and water band light pulses are then fed into a fiber delivery system (FDS) (not shown) for a subsequent surgical application.

Figure 2:
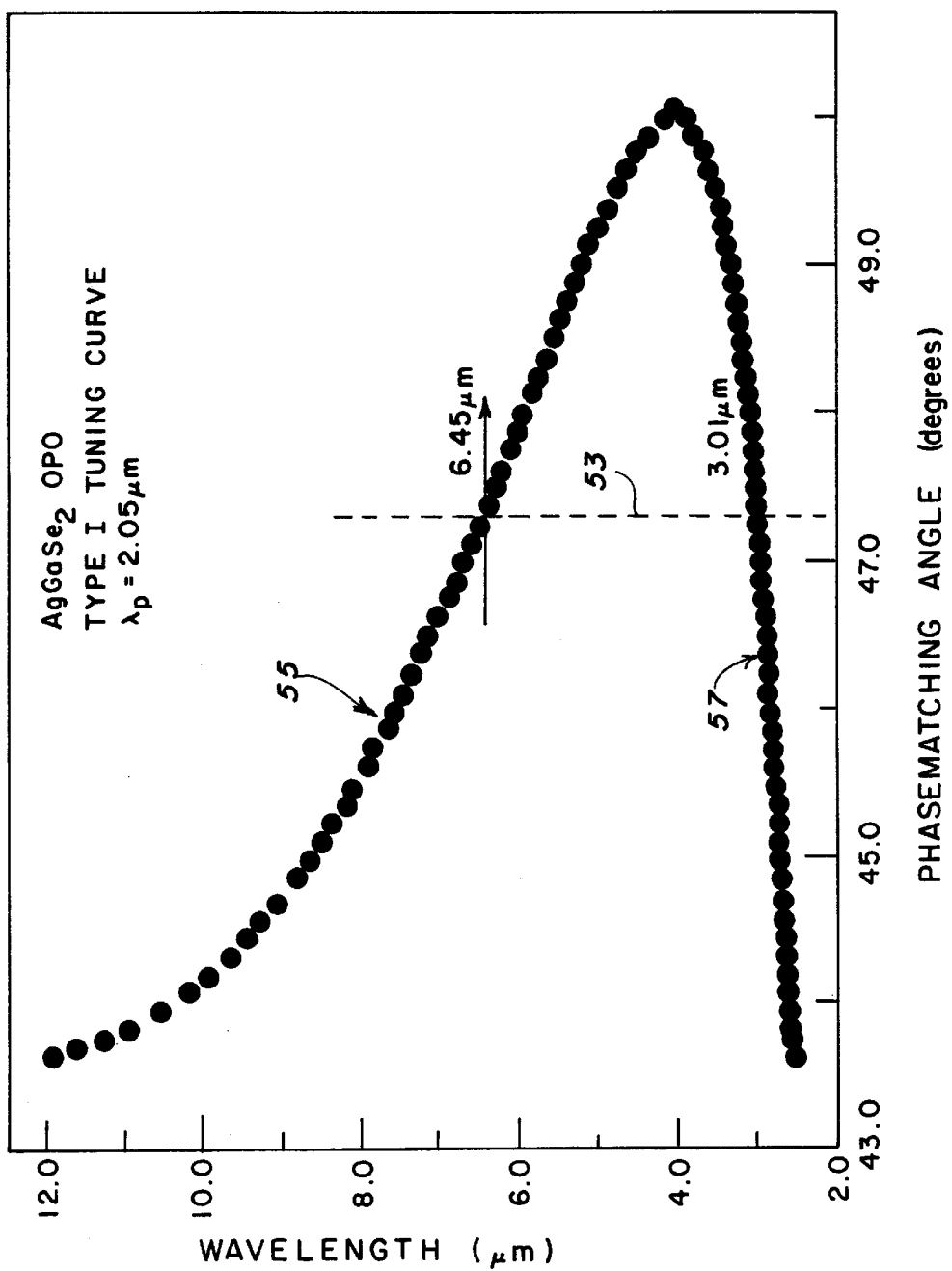
FIG. 2 shows the Type I Tuning Curve for the AgGaSe$_2$ OPO utilized in the exemplary dual wavelength surgical laser system of FIG. 1.

FIG. 2 shows angle tuning of the $AgGaSe_2$ OPO 13 pumped by the 2.05 μm output of the pump laser 11 of FIG. 1. As mentioned before, the AgGaSe2 crystal 21 is mounted on the rotation stage 23 of FIG. 1 and is angle-tuned by rotating the rotation stage 23 to a desired angle.

The diagram of FIG. 2 is known as a Type I Tuning Curve for the $AgGaSe_2$ OPO 13 utilized in the exemplary dual wavelength surgical laser system of FIG. 1. The horizontal axis represents the phasematching angle in degrees, while the vertical axis represents the wavelengths that are developed at the output of the $AgGaSe_2$ OPO 13 when the $AgGaSe_2$ crystal 21 is pumped by the 2.05 μm output of the pump laser 11 of FIG. 1. Vertical line 53 shows that for any given angle determined by the rotation of the rotation stage 23 FIG. 1 and for a particular pump wavelength, two wavelengths are selected to be outputted from the OPO 13.

More specifically, as shown by vertical line 53 in FIG. 2, when the AgGaSe$_2$ crystal 21 is rotated by the rotation stage 23 to a phase matching angle of 47.3 degrees and is pumped by the 2.05 µm pump beam, the AgGaSe$_2$ OPO 13 will produce pulses of light (or protein band light or an OPO signal line) at 6.45 µm in a protein absorption band of the tissue, as shown in an upper portion 55 of the tuning curve of FIG. 2. In addition, the OPO 13 will also produce pulses of light (or light band light or an OPO idler line) at 3.01 µm in a water absorption band of the tissue, as shown in a lower portion 57 of the tuning curve of FIG. 2. Therefore, both of the output protein and water absorption band wavelengths of the crystal 21 are determined when the crystal 21 is angle-tuned to a particular angle and pumped at a particular pump wavelength. Thus, in this example, if the phasematching angle were changed to about 47.5 degrees, the OPO 13 would develop protein absorption band light at around 6.3 µm and water absorption band light around 3.2 µm.

It should be noted at this time that, as the crystal 21 in FIG. 1 is angle-tuned by rotating the rotation stage 23 to a different phase matching angle, the wavelength of the water band light 57 shown in FIG. 2 hardly changes because of the small slope of the water band light 57. On the other hand, the wavelength of the protein band light changes quite a bit as the crystal 21 tuned, particularly at the higher end of the waveform of the protein band light 55, because of the steep slope of protein band light 55. Thus, the angle-tuning of the crystal 21 can produce only a small change in the wavelength of the water band light 57, but a relatively large change in the wavelength of the protein band light 55.

FIG. 3 is a graph illustrating the protein and water absorption lines from the OPO 13 of FIG. 1 for one exemplary tissue type, namely neural tissue, and with the tuning angle of 47.3 degrees shown in FIG. 2. The horizontal axis is shown in reciprocal centimeters or wavenumbers.

The exemplary waterband or water absorption band at around 3.01 µm is shown by an arrow 59. This water band of absorption 59 shown in FIG. 3 is quite broad. Therefore, as discussed above, as the crystal 21 of FIG. 1 is angle-tuned, the wavelength of the water band light 59 would not move out of this broad water band light 59 unless the crystal 21 is tuned very far away. It should also be noted that, as shown in FIG. 3, there is a relatively large ratio between the water tissue absorption in the 3 micron region (around 3.02 µm) and the protein tissue absorption in the 6 micron region (around 6.45 µm). Different types of tissue have a different ratio of hydration. This provides the reason why it is important to be able to adjust the ratio of the water band light to the protein band light by being able to attenuate the water band light, as discussed before.

Figure 3A:
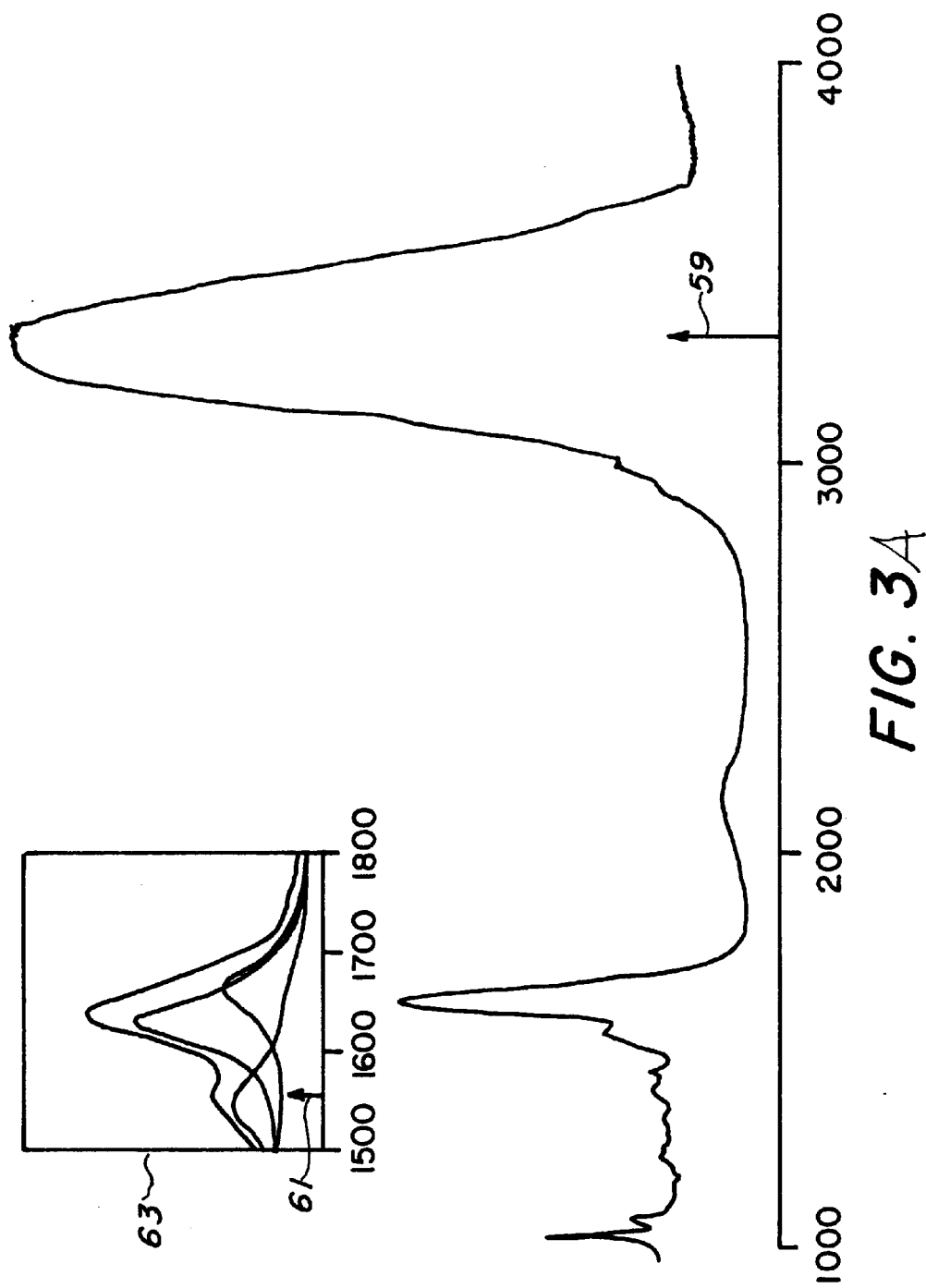
FIG. 3A shows an expanded view of a portion of the graph of FIG. 3 with three overlapping absorption bands.

As shown in FIG. 3A, the exemplary protein absorption band at around 6.45 µm is shown by an arrow 61 in an inset 63. The inset 63 shows a decomposition of the tissue into component parts due to proteins and water. So this is a water band bending mode. That is, the protein absorption bands are moving around. More particularly, inset 63 is an expanded view of of a portion of the graph of FIG. 3 with three overlapping absorption bands. Of these three overlapping bands one is a water absorption band and the other two are protein absorption bands. Since the crystal 21 is tunable, the OPO 13 can be tuned to produce a protein absorption band which does not have any water content.

It should also be noted that the OPO 13 produces a protein absorption band which has a bandwidth of about 5 wavenumbers, whereas each of the three overlapping absorption bands in the insert 6351 is about 100 wavenumbers broad. Therefore, the unrestricted protein absorptin band of the OPO 13 has adequate wavelength resolution and is adequately narrow to select one of these protein absorption bands in inset 63.

Figure 4:
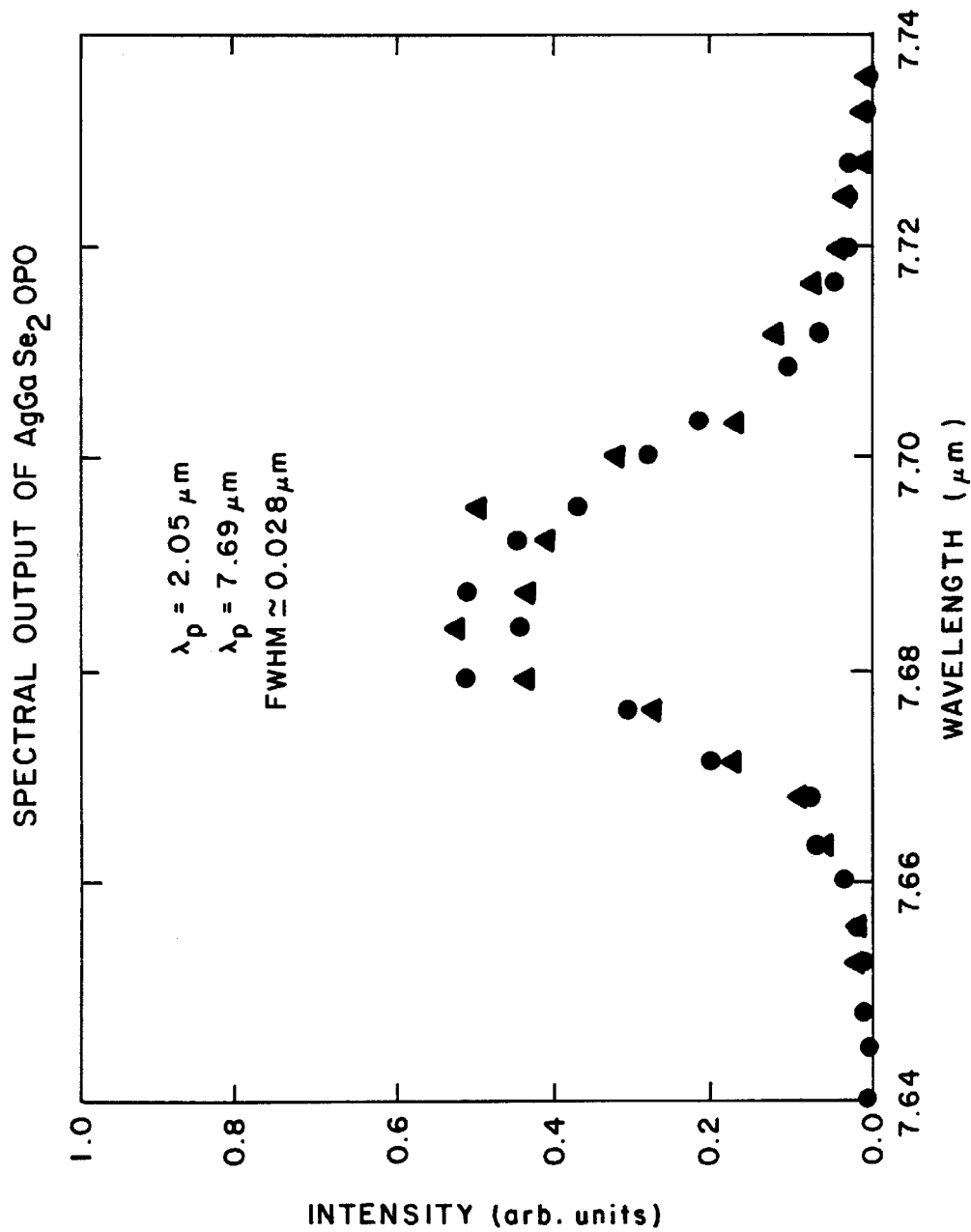
FIG. 4 is a graph showing the spectral output of the exemplary AgGaSe$_2$ OPO of FIG. 1.

FIG. 4 is a graph showing the spectral output of the exemplary AgGaSe$_2$ OPO 13 of FIG. 1. The graph in FIG. 4 shows that the simple OPO 13 of FIG. 1 has a sufficiently narrow bandwidth that operates very well to produce the desired protein and water absorption bands in response to the selected pump pulses from the pump laser 11 of FIG. 1 without requiring any linewidth restriction.

Therefore, what has been described in a preferred embodiment of the invention is a dual wavelength surgical laser system comprising: a pump laser for emitting pump laser pulses of light at a preselected pump wavelength; an optical parametric oscillator responsive to each pump pulse from the pump laser for producing a first wavelength pulse of light in a water absorption band of the tissue and a second wavelength pulse of light in a protein absorption band of the tissue; a first set of optics for only passing therethrough each first wavelength pulse from the optical parametric oscillator; an optical delay line for delaying each first wavelength pulse from the first set of optics by a predetermined period of time; a second set of optics for only passing therethrough each second wavelength pulse from the optical parametric oscillator; and a beam combiner for combining each second wavelength pulse with the following delayed first wavelength pulse to form a stream of consecutive second and delayed first pulse pairs for application to the tissue.

It should therefore readily be understood that many modifications and variations of the present invention are possible within the purview of the claimed invention. It is therefore to be understood that, within the scope of the appended claims, the invention may be practiced otherwise than as specifically described.

What is claimed and desired to be secured by Letters Patent of the United States is:

1. A dual wavelength surgical laser system for performing laser surgery on living tissue with a minimum amount of collateral tissue damage, said laser system comprising:

a pump laser for emitting pump laser pulses of light at a preselected pump wavelength of about 2 microns;

means coupled to said pump laser being responsive to each pump pulse from said pump laser for producing a first wavelength pulse of light at about 3 microns in a water absorption band of the tissue and a second wavelength pulse of light at about 6 microns in a protein absorption band of the tissue;

first optical means coupled to said producing means for only passing therethrough each first wavelength pulse from said producing means;

means coupled to said first optical means for delaying each first wavelength pulse from said first optical means by a predetermined period of time;

second optical means coupled to said producing means for only passing therethrough each second wavelength pulse from said producing means; and means coupled to said second optical means and to said delaying means for combining each second wavelength pulse with the following delayed first wavelength pulse to form a stream of consecutive second and delayed first pulse pairs for application to the tissue.

2. The dual wavelength surgical laser system of claim 1 further including:

transfer optics for sequentially transferring the pump laser pulses of light from said pump laser to said producing means with the beam size and polarization needed for desired producing means operation.

3. The dual wavelength surgical laser system of claim 1 wherein:
said producing means is an optical parametric oscillator.

4. The dual wavelength surgical laser system of claim 1 wherein:
said pump laser is a Q-switched laser.

5. The dual wavelength surgical laser system of claim 1 wherein said delaying means includes:
an adjustable optical path length optically disposed between said first optical means and said combining means.

6. The dual wavelength surgical laser system of claim 4 wherein:
said producing means is an optical parametric oscillator.

7. The dual wavelength surgical laser system of claim 6 further including:
transfer optics for sequentially transferring the pump laser pulses of light from said Q-switched laser to said optical parametric oscillator with the beam size and polarization needed for a desired operation of said optical parametric oscillator.

8. The dual wavelength surgical laser system of claim 6 wherein said delaying means includes:
an adjustable optical path length optically disposed between said first optical means and said combining means.

9. The dual wavelength surgical laser system of claim 6 wherein said optical parametric oscillator comprises:
a cavity defined by first and second reflective elements opposing each other on a common axis to form a reflective path therebetween; and
a nonlinear crystal disposed in said cavity between said first and second reflective elements, said nonlinear crystal being responsive to each pump pulse for simultaneously generating said first and second wavelength pulses.

10. The dual wavelength surgical laser system of claim 8 further including:
an attenuator disposed in an optical path between said delaying means and said combining means for attenuating the delayed first wavelength pulse to change the ratio of light in the water absorption band to the light in the protein absorption band.

11. The dual wavelength surgical laser system of claim 10 further including:
transfer optics for sequentially transferring the pump laser pulses of light from said Q-switched laser to said optical parametric oscillator with the beam size and polarization needed for a desired operation of said optical parameter oscillator.

12. The dual wavelength surgical laser system of claim 9 wherein:
said nonlinear crystal is selected from the group consisting of $AgGaSe_2$ and $ZnGeP_2$.

13. The dual wavelength surgical laser system of claim 9 further including:
a rotation stage for mounting said nonlinear crystal thereon in order to angle-tune the nonlinear crystal to produce a different associated pair of first and second wavelength pulses.

14. The dual wavelength surgical laser system of claim 13 wherein said delaying means includes:
an adjustable optical path length optically disposed between said first optical means and said combining means.

15. The dual wavelength surgical laser system of claim 14 further including:
an attenuator disposed in an optical path between said delaying means and said combining means for attenuating the delayed first wavelength pulse to change the ratio of light in the water absorption band to the light in the protein absorption band.

16. The dual wavelength surgical laser system of claim 5 further including:
an attenuator disposed in an optical path between said delaying means and said combining means for attenuating the delayed first wavelength pulse to change the ratio of light in the water absorption band to the light in the protein absorption band.

17. The dual wavelength surgical laser system of claim 16 wherein:
said pump laser is a Q-switched laser.

18. The dual wavelength surgical laser system of claim 17 wherein:
said producing means is an optical parametric oscillator.

19. The dual wavelength surgical laser system of claim 18 wherein said optical parametric oscillator comprises:
a cavity defined by first and second reflective elements opposing each other on a common axis to form a reflective path therebetween; and
a nonlinear crystal disposed in said cavity between said first and second reflective elements, said nonlinear crystal being responsive to each pump pulse for simultaneously generating said first and second wavelength pulses.

20. The dual wavelength surgical laser system of claim 19 wherein:
said nonlinear crystal is selected from the group consisting of $AgGaSe_2$ and $ZnGeP_2$.

21. The dual wavelength surgical laser system of claim 19 further including:
a rotation stage for mounting said nonlinear crystal thereon in order to angle-tune the nonlinear crystal to produce a different associated pair of first and second wavelength pulses.

22. The dual wavelength surgical laser system of claim 21 further including:
transfer optics for sequentially transferring the pump laser pulses of light from said Q-switched laser to said optical parametric oscillator with the beam size and polarization needed for a desired operation of said optical parameter oscillator.

23. The dual wavelength surgical laser system of claim 21 wherein:
said pump laser emits pump laser pulses of light at a preselected pump wavelength of about 2 microns; and
said producing means produces a first wavelength pulse of light of about 3 microns and a second wavelength pulse of light of about 6 microns.

* * * * *